United States Patent
Kaplan

(10) Patent No.: US 9,144,425 B2
(45) Date of Patent: Sep. 29, 2015

(54) SUTURE FOR SOFT TISSUE REPAIR

(71) Applicant: Lee D. Kaplan, Coconut Grove, FL (US)

(72) Inventor: Lee D. Kaplan, Coconut Grove, FL (US)

(*) Notice: Subject to any disclaimer, the term of this patent is extended or adjusted under 35 U.S.C. 154(b) by 0 days.

(21) Appl. No.: 14/514,906

(22) Filed: Oct. 15, 2014

(65) Prior Publication Data

US 2015/0032154 A1 Jan. 29, 2015

Related U.S. Application Data

(63) Continuation of application No. 14/394,351, filed as application No. PCT/US2013/063111 on Oct. 2, 2013.

(60) Provisional application No. 61/709,293, filed on Oct. 3, 2012, provisional application No. 61/792,026, filed on Mar. 15, 2013.

(51) Int. Cl.
*A61B 17/04* (2006.01)
*A61B 17/06* (2006.01)

(52) U.S. Cl.
CPC ......... *A61B 17/0401* (2013.01); *A61B 17/0487* (2013.01); *A61B 17/06166* (2013.01); *A61B 2017/0414* (2013.01); *A61B 2017/0425* (2013.01); *A61B 2017/0427* (2013.01); *A61B 2017/0448* (2013.01); *A61B 2017/0453* (2013.01); *A61B 2017/0464* (2013.01); *A61B 2017/06176* (2013.01)

(58) Field of Classification Search
CPC ............... A61B 17/0401; A61B 17/06166; A61B 17/0487; A61B 2017/0414; A61B 2017/0425; A61B 2017/0427; A61B 2017/0448; A61B 2017/0453; A61B 2017/06176; A61B 2017/0464

USPC ......... 606/228, 227, 226, 225, 224, 229, 230, 606/231, 232, 233, 139
See application file for complete search history.

(56) References Cited

U.S. PATENT DOCUMENTS

| | | | |
|---|---|---|---|
| 7,445,634 B2 | 11/2008 | Trieu | |
| 8,202,295 B2 | 6/2012 | Kaplan | |
| 8,231,653 B2* | 7/2012 | Dreyfuss | 606/232 |
| 2005/0192631 A1* | 9/2005 | Grafton | 606/228 |
| 2006/0079904 A1* | 4/2006 | Thal | 606/72 |
| 2008/0077161 A1 | 3/2008 | Kaplan | |
| 2008/0249567 A1* | 10/2008 | Kaplan | 606/232 |
| 2009/0248067 A1* | 10/2009 | Maiorino | 606/228 |
| 2010/0114162 A1 | 5/2010 | Bojarski et al. | |

(Continued)

OTHER PUBLICATIONS

International Search Report and Written Opinion in International Application No. PCT/US2013/063111 mailed Mar. 18, 2014 (12 pages).

*Primary Examiner* — Katrina Stransky
(74) *Attorney, Agent, or Firm* — Foley & Lardner LLP

(57) ABSTRACT

A method for repairing a soft tissue includes boring a first nest in a portion of a bone at a first location, boring a second nest through a portion of the bone at a second location, shuttling a suture from a top surface of the soft tissue to a bottom surface of the soft tissue, disposing a first suture anchor in the first nest and fixating the first suture anchor to the first location, passing the suture through the first suture anchor, the bottom surface of the soft tissue and the top surface of the soft tissue to form a medial row, disposing a second suture anchor in the second nest and fixating the second suture anchor to the second location, passing the suture through the second suture anchor from the top surface of the soft tissue to form a lateral row, and tensioning the suture.

13 Claims, 19 Drawing Sheets

(56) References Cited

U.S. PATENT DOCUMENTS

| | | |
|---|---|---|
| 2012/0165869 A1 | 6/2012 | Kaplan |
| 2012/0197294 A1 | 8/2012 | Martin |
| 2012/0239088 A1 | 9/2012 | Kaplan |
| 2012/0245629 A1 | 9/2012 | Gross et al. |
| 2012/0245634 A1 | 9/2012 | Kaplan |
| 2013/0023928 A1* | 1/2013 | Dreyfuss ................ 606/228 |
| 2013/0345749 A1* | 12/2013 | Sullivan et al. ........... 606/232 |
| 2014/0039551 A1* | 2/2014 | Donahue ................ 606/232 |

\* cited by examiner

SUTURE FOR SOFT TISSUE REPAIR

CROSS REFERENCE TO RELATED APPLICATIONS

This application is a continuation of U.S. Non-Provisional application Ser. No. 14/394,351, filed on Oct. 14, 2014, which is a national stage application of International Application Serial No. PCT/US2013/063111, filed on Oct. 2, 2013, which claims the benefit of U.S. Provisional Application Nos. 61/709,293, filed on Oct. 3, 2012, and 61/792,026, filed on Mar. 15, 2013, all of which are hereby incorporated by reference in their entirety, for any and all purposes.

FIELD

The present disclosure generally related to a suture for soft tissue repair. More specifically, the disclosure relates to suture configurations for more effectively securing tissue and a system and method for double-row, knotless soft tissue repair.

SUMMARY

In a first aspect, a system for repairing a soft tissue includes a first suture anchor, a suture and a second suture anchor. The first suture anchor is disposed at a first location on a bone. The suture is defined by a first end and a second end. The second suture anchor disposed at a second location on the bone. The suture is passed through the first suture anchor and the second suture anchor to form a medial row and a lateral row to repair the soft tissue.

In a second aspect, an asymmetric suture for soft tissue repair is provided. The asymmetric suture includes a first region proximate to a first end of the asymmetric suture, a second region, and a third region proximate to a second end of the asymmetric suture. The first region has a first width, the second region has a second width and the third region has a third width. The second width is greater than the first and the third widths.

In a third aspect, a method for repairing a soft tissue includes boring a first tunnel through a portion of a bone at a first location and boring a second tunnel through a portion of the bone at a second location. A suture is shuttled from a top surface of the soft tissue to a bottom surface of the soft tissue. A first suture anchor is disposed in the first tunnel and fixated to the bone at the first location. The suture is passed through the first suture anchor, the bottom surface of the soft tissue and the top surface of the soft tissue to form a medial row. A second suture anchor is disposed in the second tunnel and fixated to the bone at the second location. The suture is passed through the second suture anchor from the top surface of the soft tissue to form a lateral row. The suture is tensioned with the second suture anchor.

In a fourth aspect, a kit is provided. The kit includes a suture, a first suture anchor configured to allow for the suture to move through the anchor in at least one direction and a second suture anchor configured to secure the suture.

In a fifth aspect, a suture loop includes a compressible material formed into a circular shape having a first half and a second half and a plurality of teeth provided along an interior circumference of the compressible material. The compressible material is configured to receive a suture. The compressible material is configured to compress upon itself such that the teeth provided along the interior circumference of the first half engage with the teeth provided along the interior circumference of the second half to secure the suture.

In a sixth aspect, a suture for soft tissue repair includes a first region proximate to a first end of the suture, the first region having a plurality of teeth, a second region, and a third region proximate to a second end of the suture, the third region having a plurality of teeth. When the suture is tied in a loop, the plurality of teeth of the first region is configured to engage the plurality of teeth of the second region to secure the second region of the suture.

DESCRIPTION

Figure 1A:
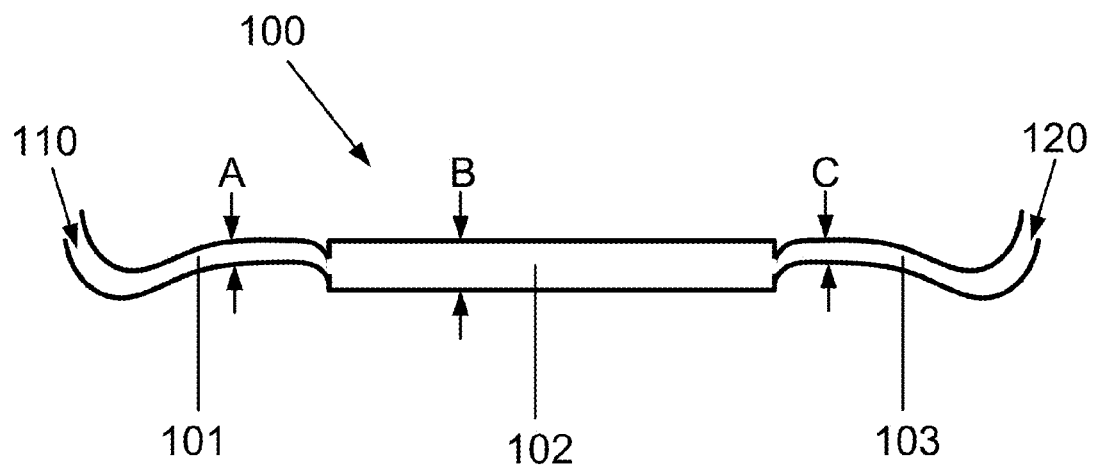
FIGS. 1A-1E are top view illustrations of alternate configurations of an asymmetric suture, according to alternative embodiments.
Figure 1B:
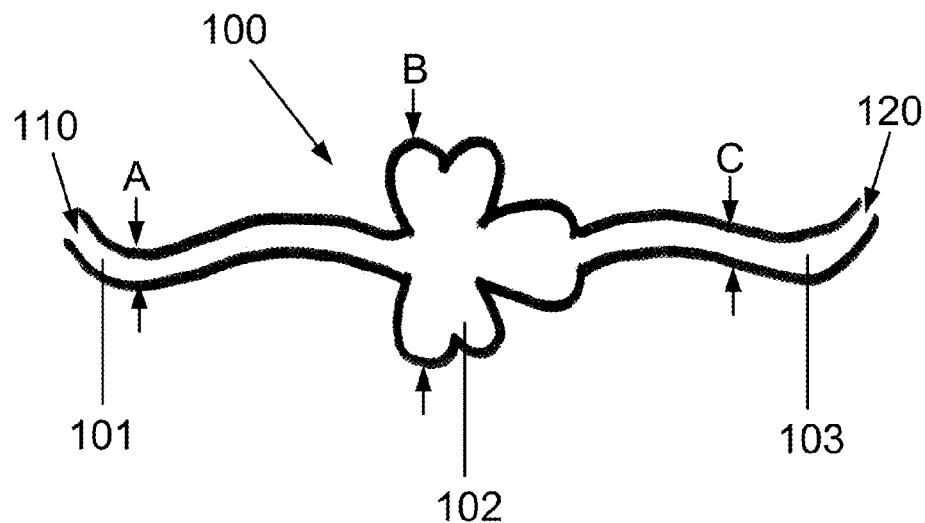
Figure 1C:
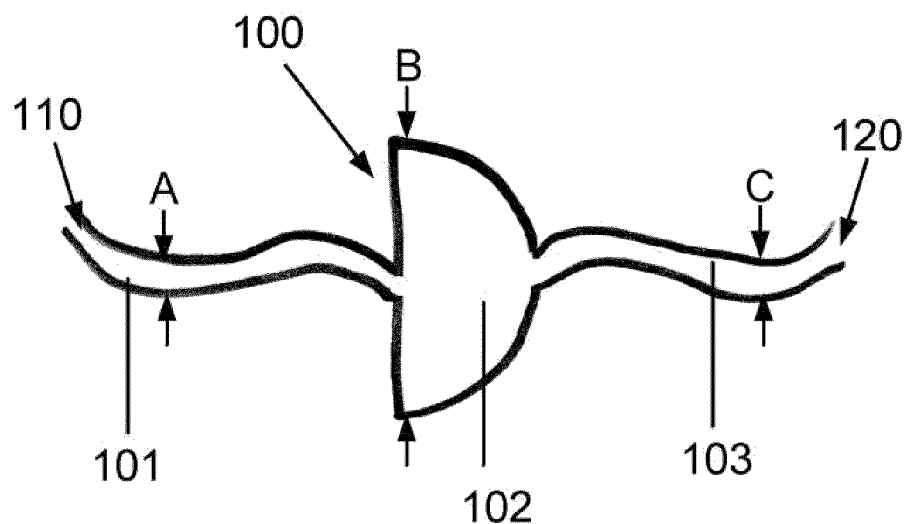
Figure 1D:
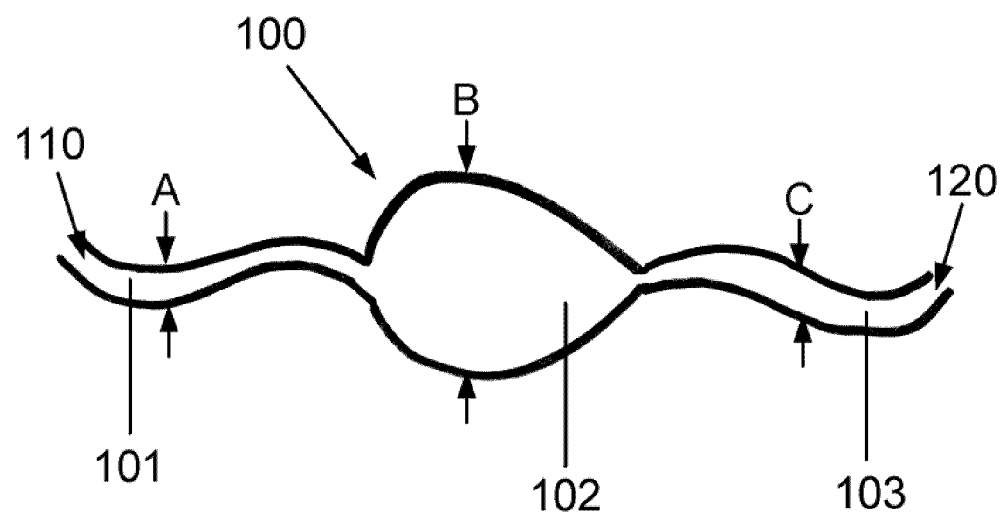
Figure 1E:
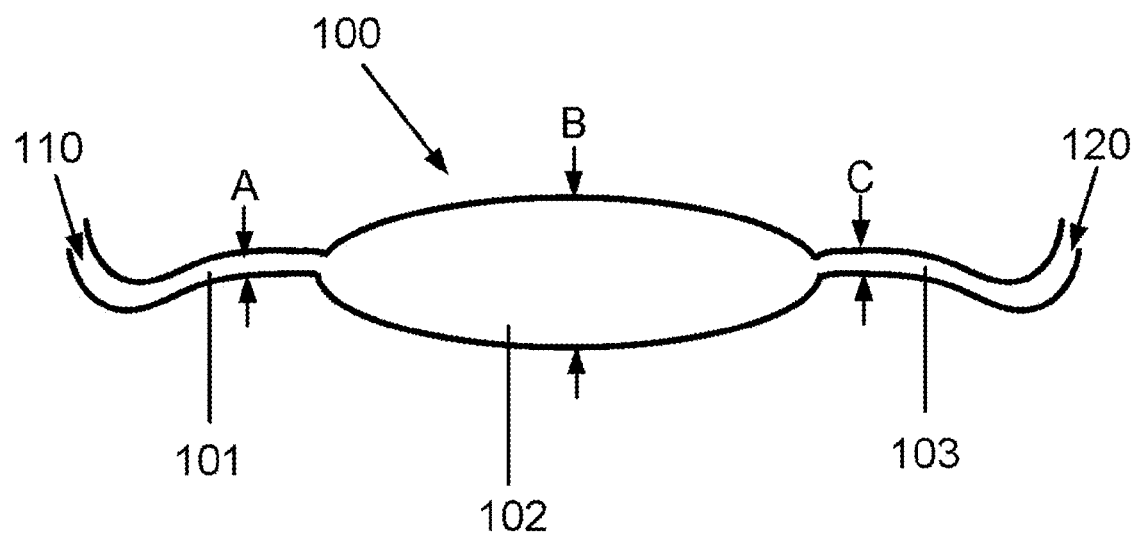

In one aspect, a system for double-row, knotless soft tissue repair includes a suture, a first suture anchor, and a second suture anchor. As used herein, the term "double-row" refers to a suture configuration including a medial row and a lateral row. The term "medial row" refers to the suture medially passing through the soft tissue from a bottom surface of the soft tissue (i.e., a surface closest to a bone) to a top surface of the soft tissue. The term "lateral row" refers to the suture laying across the top surface of the soft tissue from a first point on the top surface to a second point on the top surface. The term "knotless" refers to an aspect of the system in which it is unnecessary to tie a knot in the suture between the medial row and the lateral row.

Referring now to FIGS. 1A-1E, in one embodiment, the suture 100 may be any suture known to those of skill in the art. In a preferred embodiment, the suture 100 is an asymmetric suture with a length defined by a first limb 110 and a second limb 120. The suture 100 includes a first region 101 having a width A, a second region 102 having a width B, and a third region 103 having a width C. The first region 101 is disposed at the first limb 110, the third region 103 is disposed at the second limb 120, and the second region 102 is disposed between the first limb 110 and the second limb 120. The first, second and third regions 101-103 are continuously formed such that the suture 100 is a single piece. The width B of the second region 102 is greater than the width A of the first region 101 and the width C of the third region 103. The widths A and C may be the same, for example, the width of a conventional suture known to those of skill in the art. Transitions from the first to the second regions of any asymmetric suture and from the second to the third regions of any asymmetric suture anchor may be well-defined, blocked transitions, they may be graduated, or smooth gradient transitions, or any type or shape of transition in between.

The length of the suture 100 and each of the regions 101-103 are predetermined such that when the suture 100 is used for a double-row, knotless repair of a soft tissue, the second region 102, having the width B wider than that of a conventional suture, is disposed on a surface of the soft tissue and forms the lateral row. The second region 102 of the suture 100 provides a greater contact area between the suture 100 and the soft tissue that may even the distribution of pressure on the soft tissue and more effectively hold the soft tissue down to the bone in a manner similar to the true native footprint of the bone and the soft tissue in a natural state, prior to the damage to the tissue that is being repaired.

Figure 20:
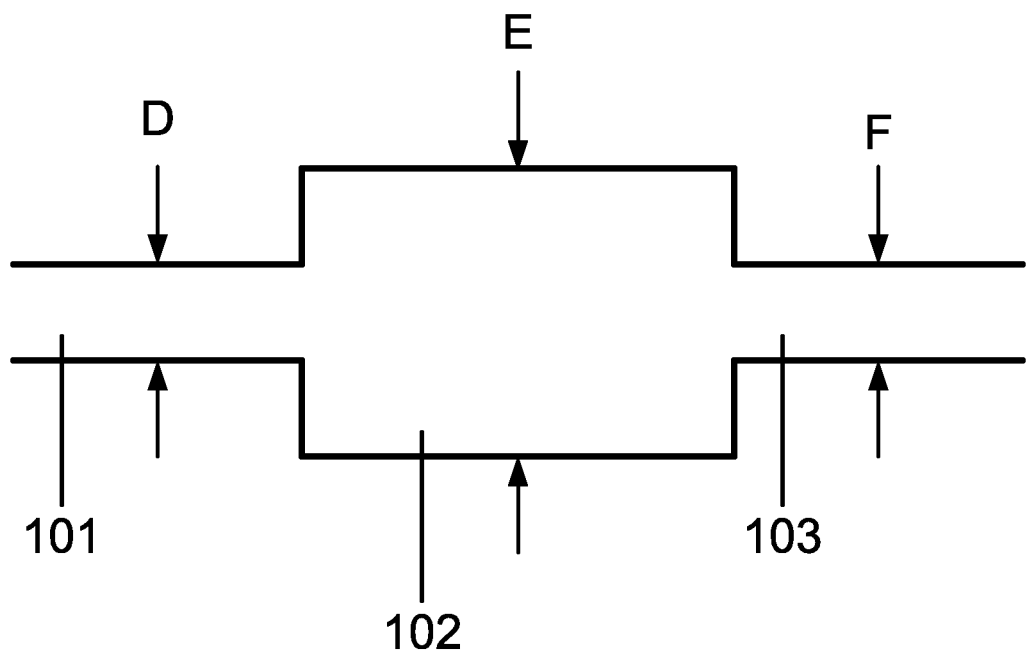
FIG. 20 is a side view of an asymmetric suture, according to one embodiment.

In some embodiments, the first region 101, the second region 102 and the third region 103 may have a thickness D, a thickness E, and a thickness F, respectively (see FIG. 20). The thickness E of the second region 102 may be greater than the thickness D of the first region 101 and the thickness F of the third region 103. The thicknesses D and F may be the same, for example, the thickness of a conventional suture known to those of skill in the art. In one embodiment, the greater thickness E of the second region 102 is achieved by forming the second region 102 of a reinforced or different material from a material used to form the first region 101 and the third region 103.

The second region 102 of the asymmetric suture 100 may have any suitable shape (see, for example, FIGS. 1A-1E). For example, the second region 102 may have a shape of a rectangle, an ellipse, a clover, a tear drop, or a semicircle. Alternatively, the second region 102 may be custom molded to fit the contours of the tissue being repaired. This list of shapes has been presented for purposes of illustration and of description. It is not intended to be exhaustive or limiting with respect to other shapes that may be utilized for the second region 102.

Figure 19:
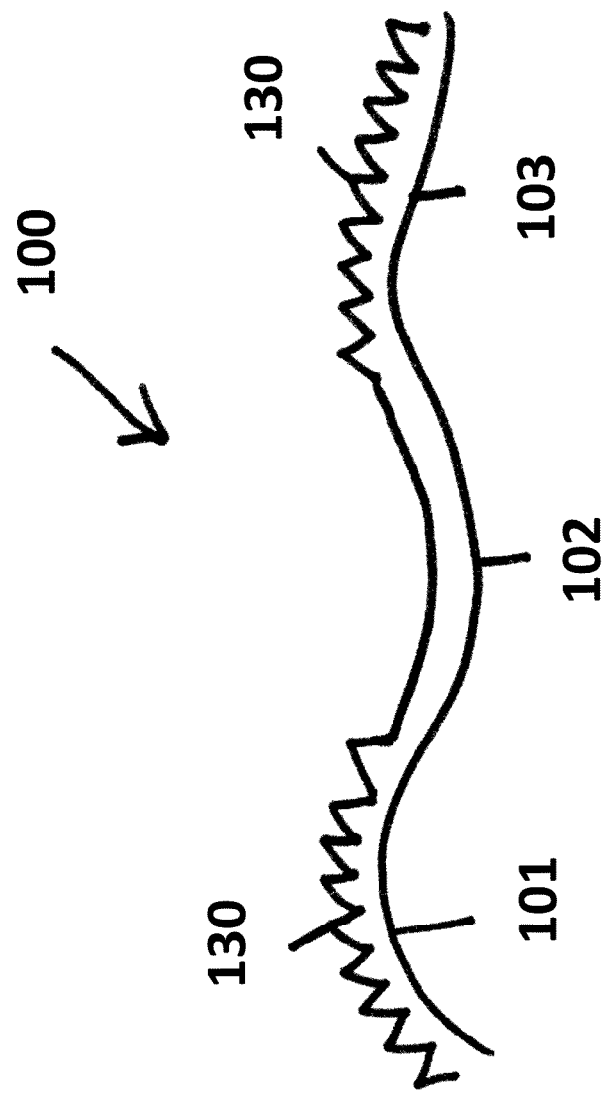
FIG. 19 is an illustration of a suture provided with teeth at ends of the suture, the teeth configured to secure a portion of the suture that does not have teeth.

In one embodiment, as illustrated in FIG. 19, the first region 101 and the third region 103 may include a plurality of teeth 130 such that when the suture 100 is tied in a knot or a loop, the teeth 130 of the first region 101 and the third region 103 come into contact and clamp down on the second region 102 to secure the suture 100. In this embodiment, the widths A, B and C of the first, second and third regions 101, 102 and 103 may be the same or different. Similarly, the thicknesses D, E and F of the first, second and third regions 101, 102 and 103 may be the same or different.

Figure 17:
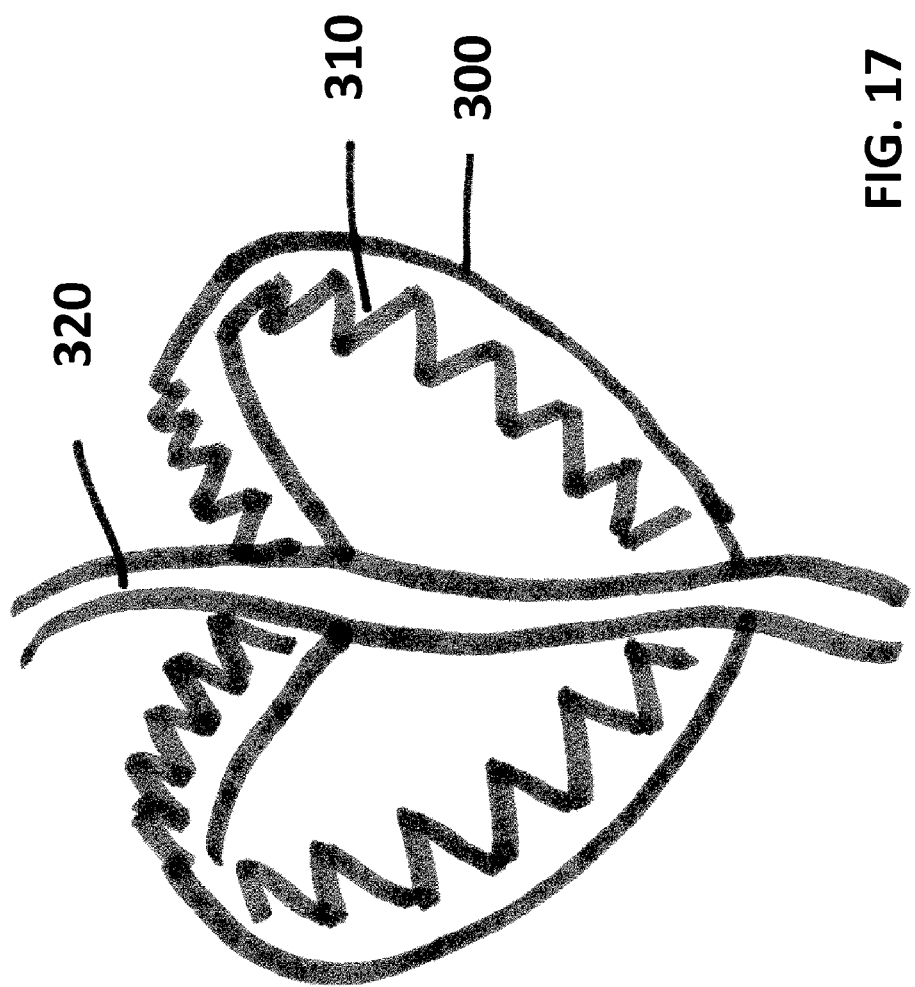
FIG. 17 is an illustration of a loop provided with teeth to secure a suture.
Figure 18:
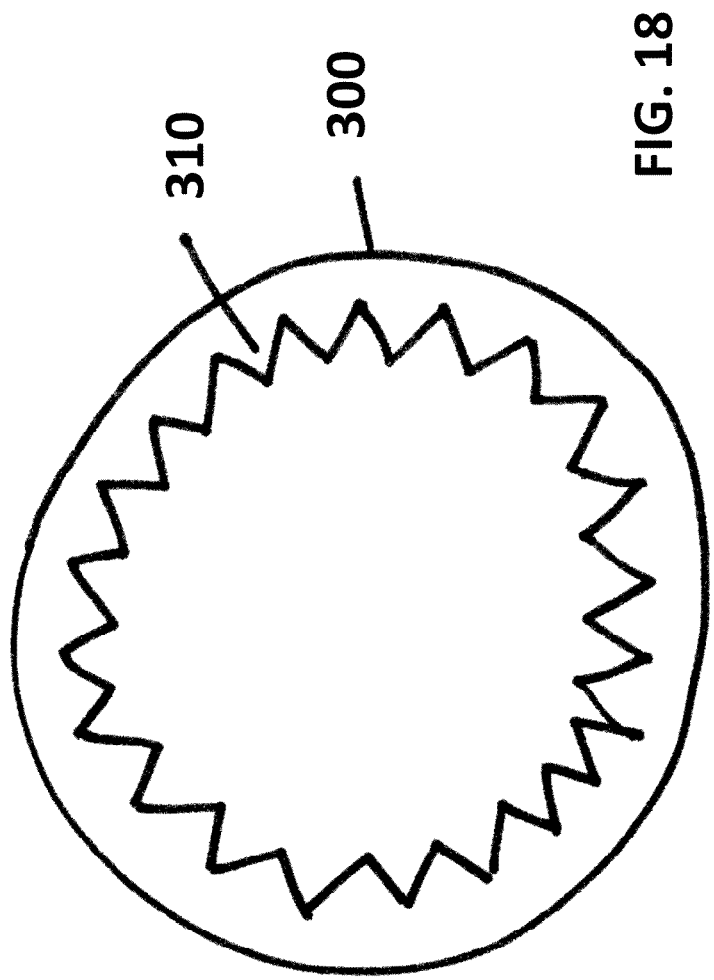
FIG. 18 is an illustration of the loop of FIG. 17 without a suture.

Referring to FIGS. 17 and 18, a loop 300 may be used in conjunction with any known medical devices or applications that involve suturing. For example, the loop 300 may be disposed within a suture anchor, may be looped within another suture, may be looped within a mesh, for example, a mesh utilized for hernia repair, or may be sutured to a piece of hardware such as an orthopedic impact rod or hardware used in a joint replacement.

The loop 300 is configured to receive and secure a suture 320. In one embodiment, the loop 300 includes a plurality of teeth 310 disposed along an inner circumference of the loop 300. Although FIGS. 17 and 18 illustrate that the teeth 310 are disposed along an entire circumference of the loop 300, the teeth 310 may be disposed in only portions of the circumference of the loop 300 in other embodiments. In further embodiments, the loop 300 does not include teeth 310.

When a suture 320 is received in the loop 300, the suture 320 may be slid back and forth until a desired position is achieved. The suture 320 may have a shape or size corresponding to any of the embodiments of suture 100 described above. The suture 320 may be passed through skin or tissue, looped upon itself, and tightened according to any known methods for using and applying a suture. Once the suture 320 is tightened, for example, by pulling both ends of the suture 320, the teeth 310 clamp down on the suture 320, in a manner akin to the operation of a bear trap, in order to secure the suture 320. In embodiments in which the loop 300 includes teeth 310, the suture 320 is secured when teeth 310 provided at a first portion of the loop 300 engages with teeth 310 provided at a second portion of the loop 300, opposite to the first portion. In embodiments in which the loop 300 does not include teeth, the suture 320 is secured when the first portion of the loop engages with the second portion of the loop, opposite to the first portion.

The loop 300 will lock the suture 320 in place when the loop 300 clamps down on the suture 320. In embodiments in which the loop 300 includes teeth 310, the teeth 310 may be permanently engaged or the teeth 310 may only engage when the suture 320 is tied. In an embodiment in which the teeth 310 are not permanently engaged, the loop 300 allows for tightening, adjustment, or re-tensioning of a suture by loosening the teeth 310, adjusting or re-tensioning of the suture 320, and re-clamping the teeth 310. For example, the loop 300 may be configured such that the application of pressure along a direction in which the suture 320 passes loosens or unclamps the teeth 310. Such loops also allow for securing of the suture without the tying of knots or replacement of sutures when re-tensioning is required. The first limb of the suture 320 may be secured in a first suture anchor 200 (i.e., a medial row suture anchor as described in further detail below) via the loop 300. A second limb of the suture 320 may be secured in a second suture anchor 250 (i.e., a lateral row suture anchor as described in further detail below).

Loops 300 may be made from a variety of materials known to those of skill in the art. In an exemplary embodiment, the loop 300 is made from materials that may be compressed. In such embodiments, the loop material is capable of being compressed from an uncompressed state to a compressed state, prior to or during clamping of the teeth 310 to the suture 320. Such compression allows for the material to recoil from the compressed state to the uncompressed state. Such materials that may be compressed include, but are not limited to, polyethylenes, silicones, polyesters, polyurethanes, polylactic acid, polyglycolic acid, or a blend of any two or more such materials. Any material utilized must be biocompatible. As used herein, biocompatible is intended to mean that the material is intended for placement in a patient or subject and will not cause deleterious effects in the patient.

Loops 300 may be used in conjunction with devices for the fixation of soft tissue to bone, or of bone to bone. This will be described in further detail below. Alternatively, the loop 300 may be used to secure sutures tensioning tissue without tissue to bone direct contact. Examples of such uses of suture tensioning without tissue to bone contact include, but are not limited to, pelvic surgery, bladder suspension surgery, brow lift or face lift surgery, hand surgery and the like.

Although the loop 300 is illustrated as having a generally circular shape, the loop 300 may be in the form of other shapes, for example, elliptical, tear-drop shaped, etc. Any suitable shape can be utilized, provided the loop 300 is capable of collapsing upon itself to secure the suture 320.

In an embodiment described by FIG. 19, the suture 100 may be passed through skin or tissue, looped upon itself, and tightened according to any known methods for using and applying a suture. In one embodiment, when the suture 100 is looped upon itself, the suture 100 pulls on a third region 103 to collapse the third region 103 upon the first region 101. Once the suture 100 is tightened, the teeth 130 of the first region 101 and the third region 103 engage to clamp down on the suture 100, in a manner akin to the operation of a bear trap, in order to secure the suture 100.

In one embodiment, the suture 100 may include a plurality of first limbs 110 and a plurality of second limbs 120. The plurality of first limbs 110 may be secured by a single first suture anchor 200 or by a plurality of first suture anchors 200. Similarly, the plurality of second limbs 120 may be secured by a single second suture anchor 250 or by a plurality of second suture anchors 250. According to this configuration, the second region 102 may be pulled down and secured in multiple locations of the second region 102 by the plurality of first limbs 110 and the plurality of second limbs 120.

Figure 2:
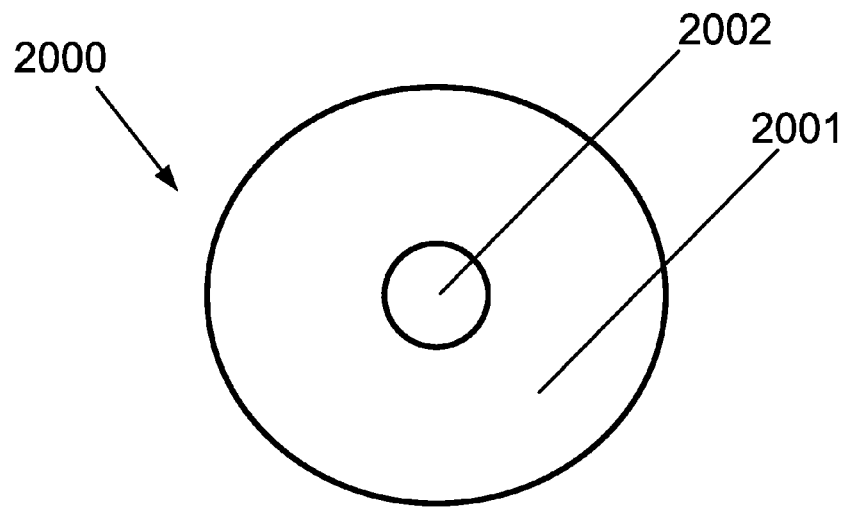
FIG. 2 is a front view of a first suture anchor, according to one embodiment.
Figure 3:
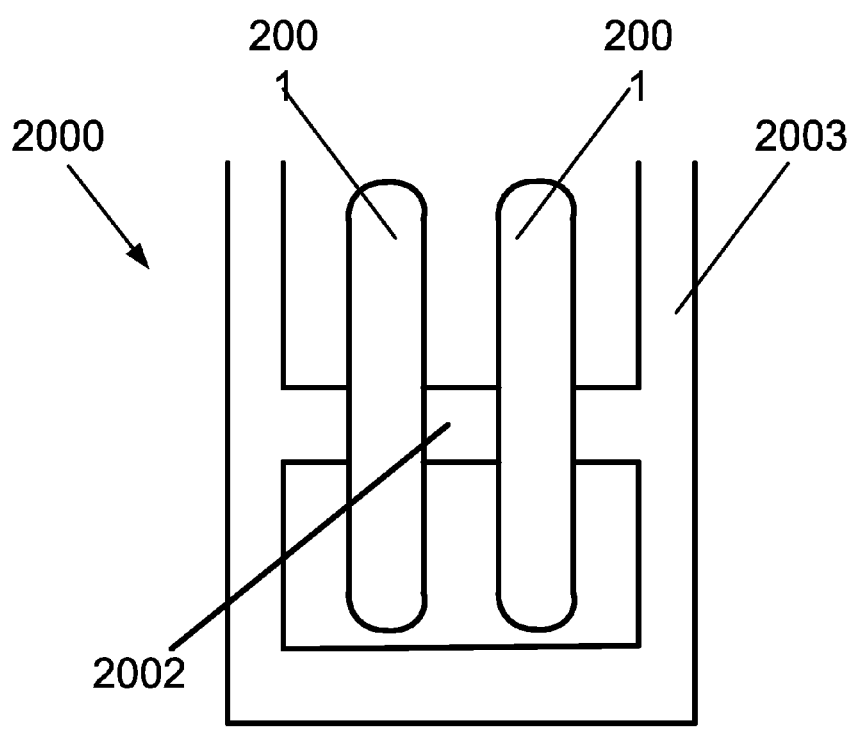
FIG. 3 is a side view of the first suture anchor, according to the embodiment of FIG. 2.
Figure 4:
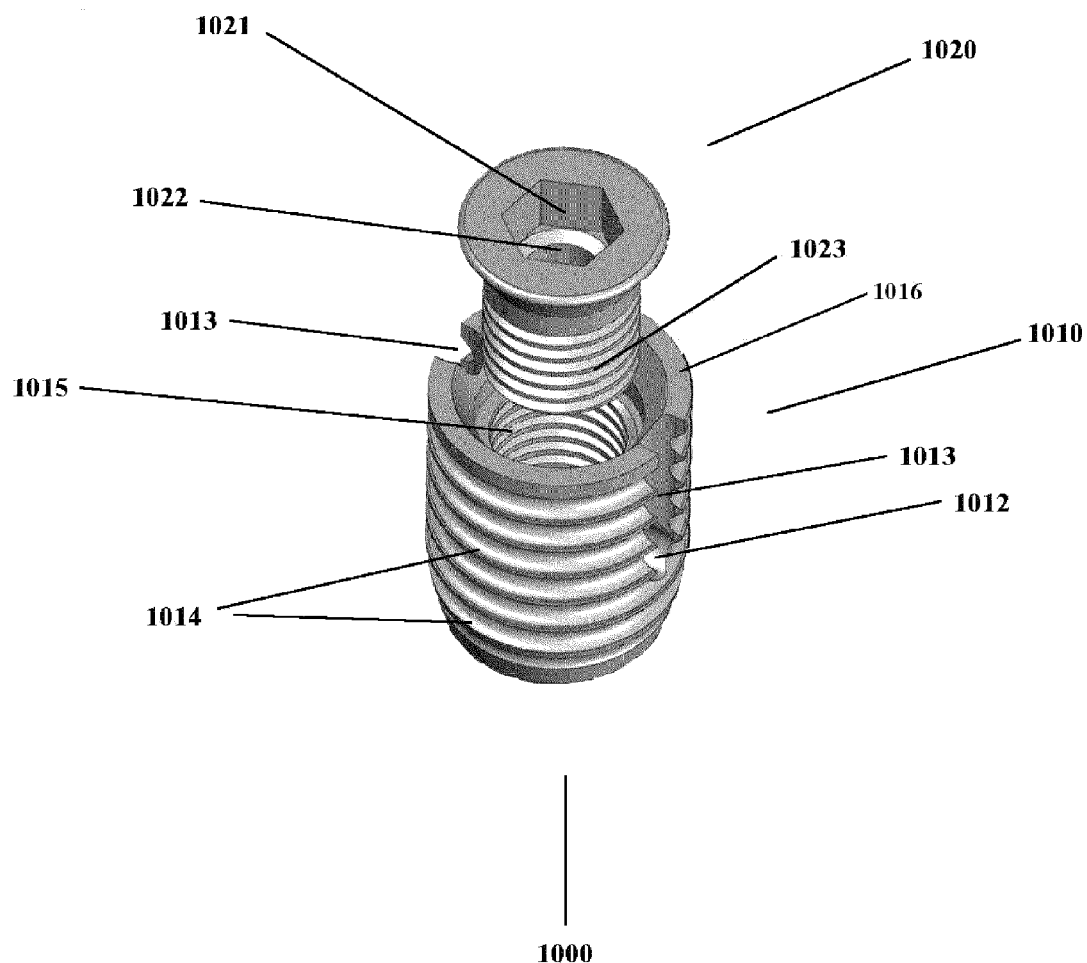
FIG. 4 is a perspective view of a second suture anchor, according to one embodiment.
Figure 5:
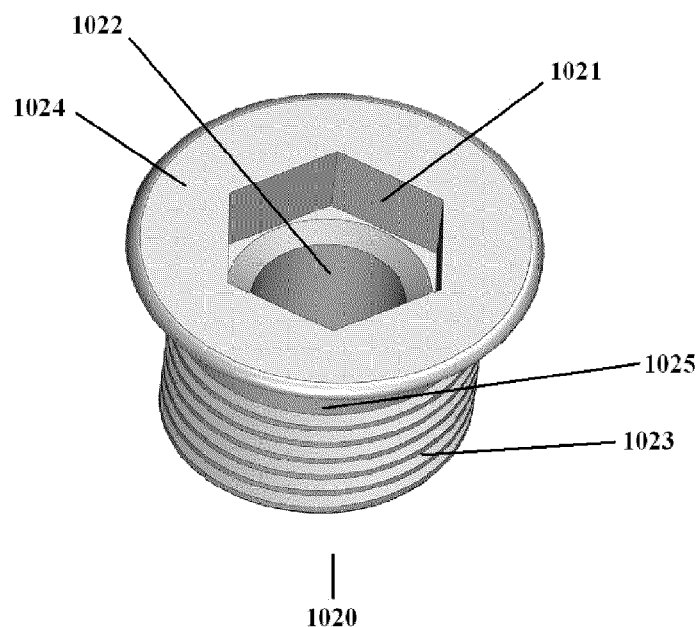
FIG. 5 is a perspective view of an anchor plug of the suture, according to the embodiment of FIG. 4.
Figure 6:
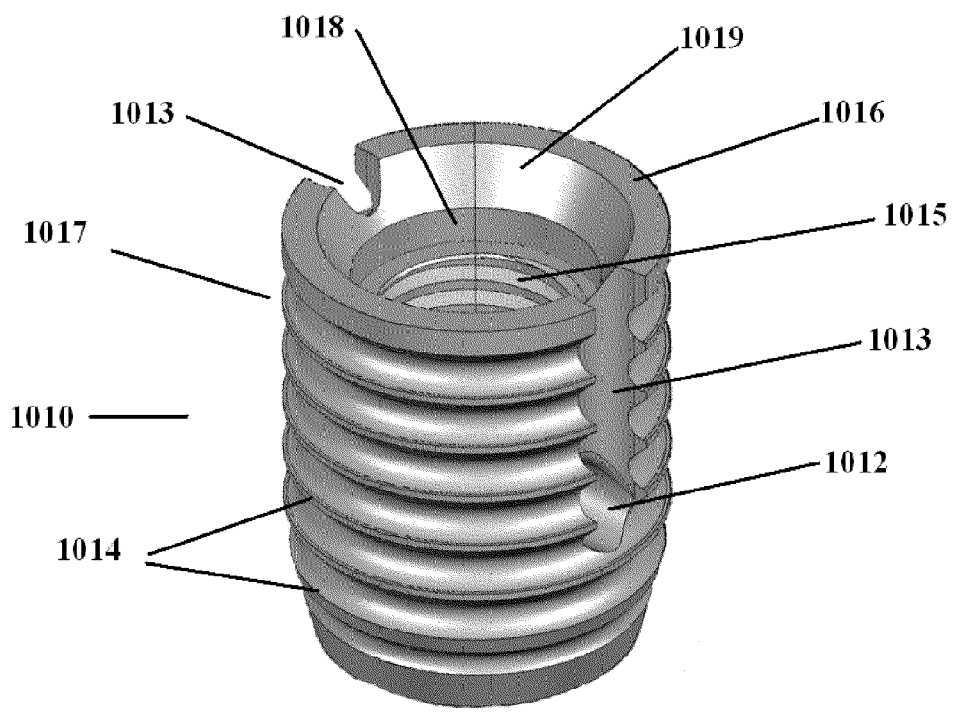
FIG. 6 is a perspective view of an anchor body of the second suture anchor, according to the embodiment of FIG. 4.
Figure 7:
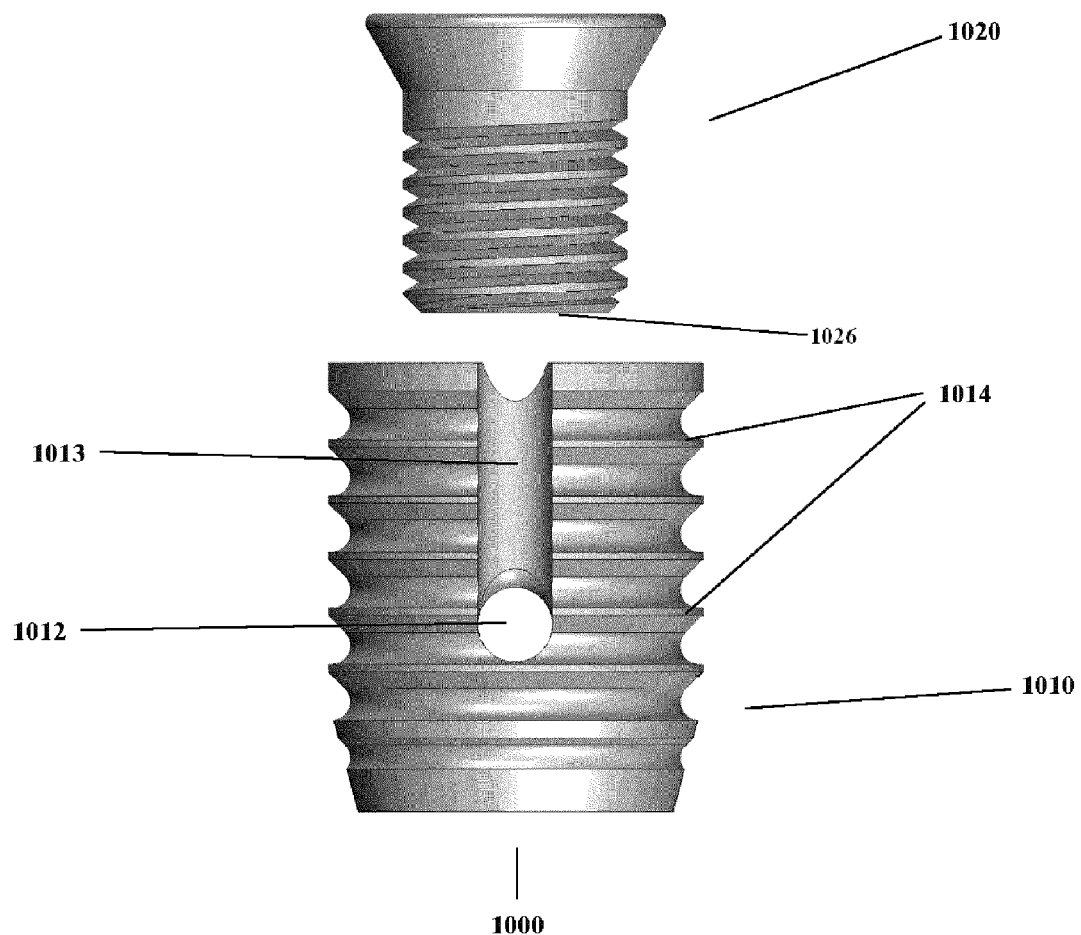
FIG. 7 is a side view of the second suture anchor, according to the embodiment of FIG. 4.

A system for double-row, knotless soft tissue repair includes a suture 100, a first suture anchor 200, and a second suture anchor 250. The first suture anchor 200 and the second suture anchor 250 may be any suture anchor known to those of skill in the art. In one embodiment, the first suture anchor 200 is a pulley anchor 2000 including two discs 2001 connected by an axle 2002 that traverses a hole disposed in a center of each disc 2001, as illustrated in FIGS. 2-3. The axle 2002 may be connected to a housing 2003. The suture 100 wraps around the axle 2002 along a direction of clockwise rotation of the discs 2001. A tension of the suture 100 may be altered according to movement of the suture 100 along the axle 2002. The suture 100 is not locked in that the suture 100 may be pulled in a first direction, along a direction of clockwise rotation of the discs 2001, and in a second direction, opposite to the first direction, along a direction of counterclockwise rotation of the discs 2001.

Figure 13:
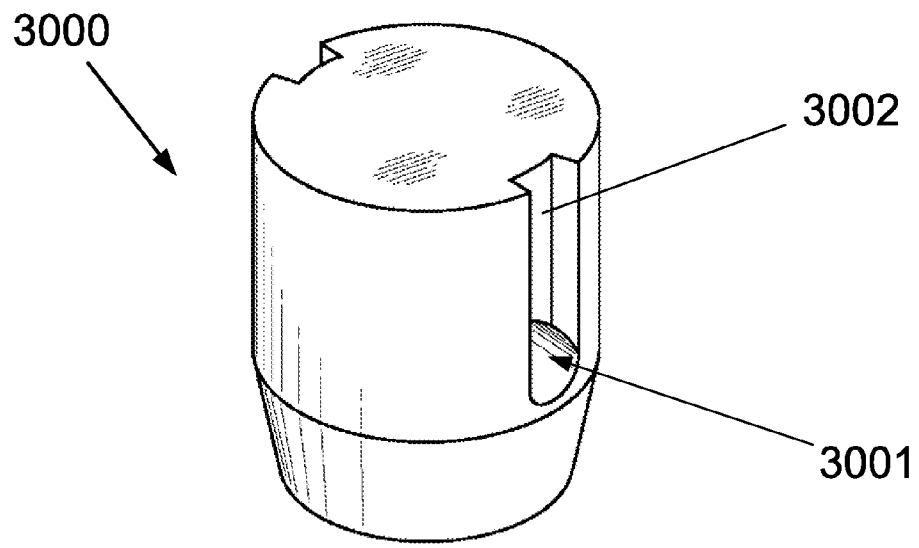
FIG. 13 is an isometric view of a first suture anchor, according to a second embodiment.
Figure 14:
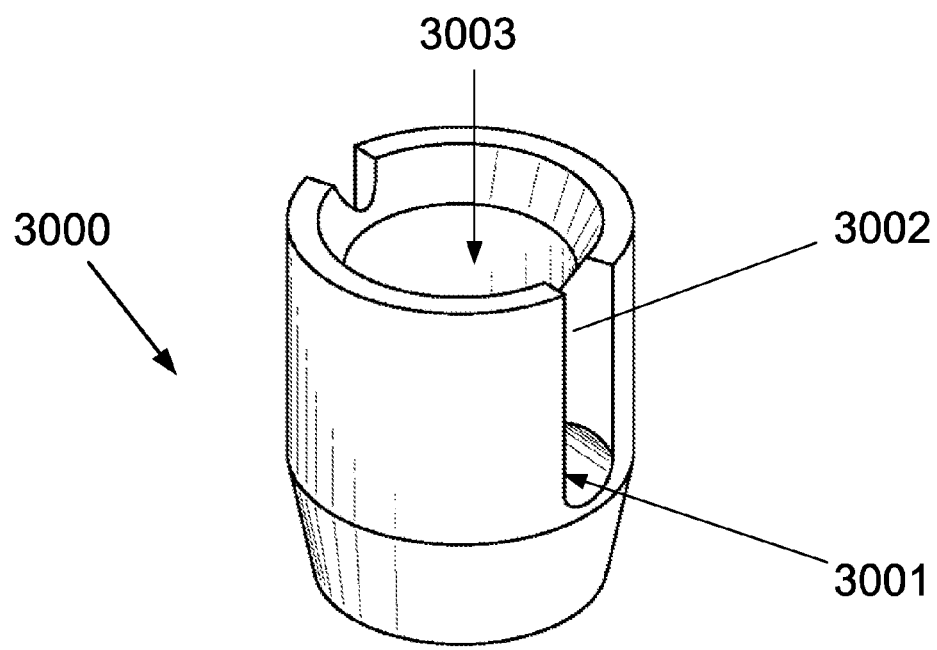
FIG. 14 is an isometric view of the first suture anchor, according to the embodiment of FIG. 13, with a central open portion.

In another embodiment, as illustrated in FIGS. 13-14, the first suture anchor 200 is a suture anchor 3000 having a transverse bore 3001 such that a suture may be fed through the bore 3001 and the suture is slidable within the bore 3001. The first suture anchor 3000 may also include channels 3002 in an outer surface of the suture anchor 3000 which are in communication with the bore 3001, such that the suture is slidable within the channels 3002 and the bore 3001. The first suture anchor 3000 may be solid with the exception of the transverse bore (see FIG. 13) or may include a central open portion 3003 (see FIG. 14).

Figure 15:
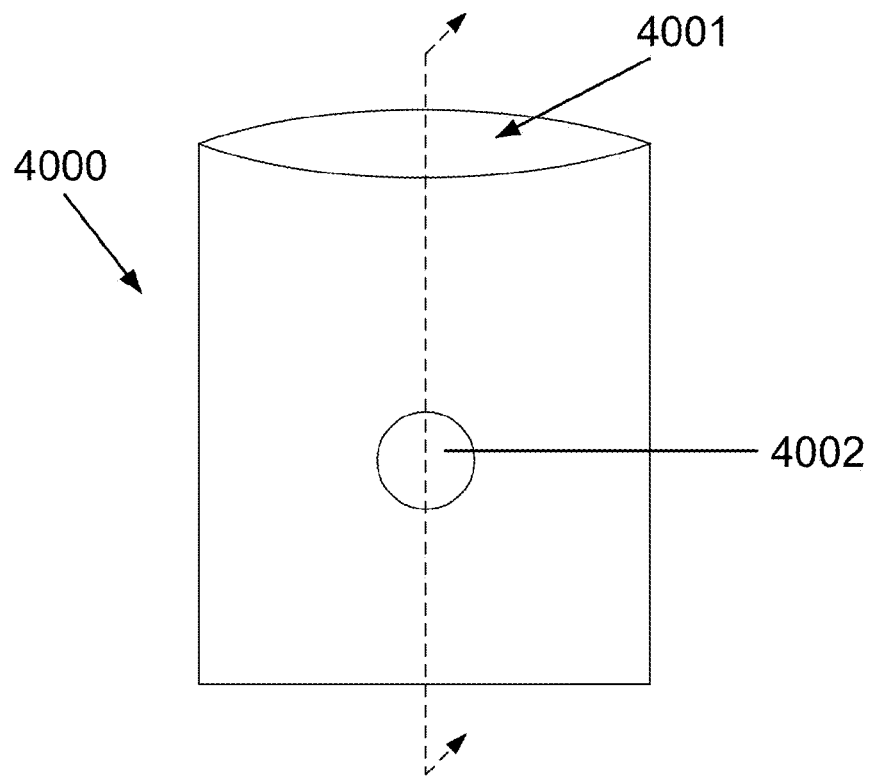
FIG. 15 is a side view of a first suture anchor, according to a third embodiment.
Figure 16:
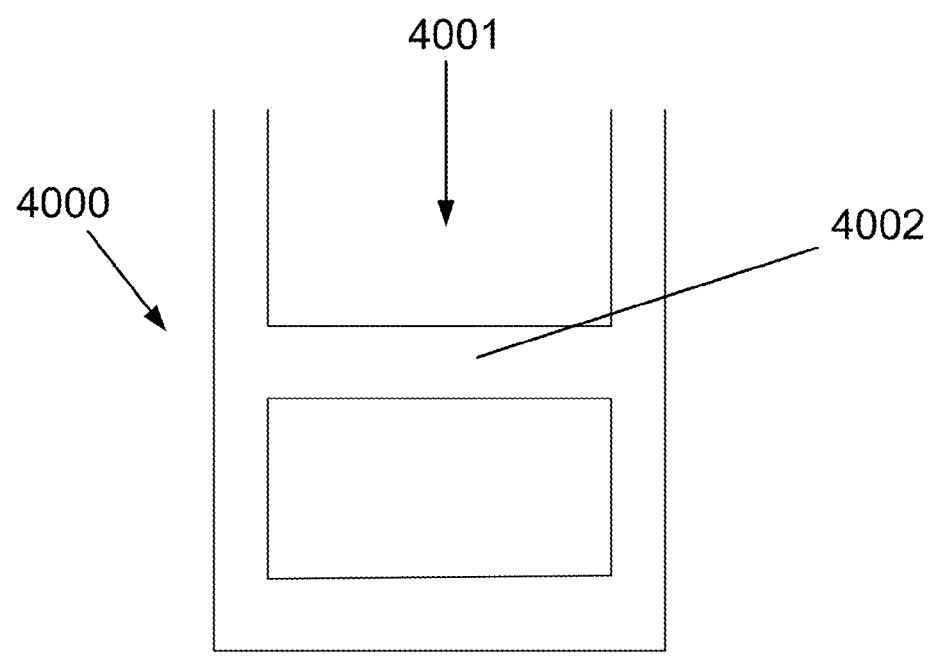
FIG. 16 is a front, cross-sectional view of the first suture anchor, according to the embodiment of FIG. 15.

In another embodiment, as illustrated in FIG. 15, the first suture anchor 200 is a suture anchor 4000 including an internal bore 4001 defining a longitudinal bore along an insertion axis of the suture anchor 4000, and a transverse post 4002. In such an embodiment, a suture may be fed into the internal bore 4001, passed under the transverse post 4002, and exited from a top portion of the suture anchor 4000, such that the transverse post 4002 serves as a pulley or slide for the suture.

The first suture anchor 200 may be made from a variety of materials known to those of skill in the art. For example, for the first suture anchor the material is typically a rigid material such as a metal, a polymer, or a ceramic. Biocompatible metals include, but are not limited to stainless steel, titanium, tantalum, aluminum, chromium, molybdenum, cobalt, silver, and gold, or alloys of such metals that are known to those of skill in the art. Biocompatible polymers include, but are not limited to, high-density polyethylenes, polyurethanes, or blends of such polymers, as are known to those of skill in the art. Biocompatible polymers also include absorbable materials such as polylactic acid, polyglycolic acid, or mixtures thereof. Biocompatible ceramics include, but are not limited to alumina, silica, silicon carbide, silicon nitride, zirconia, and mixtures of any two or more thereof.

In other embodiments, the suture 100 is locked or prevented from being pulled back in the second direction after the suture 100 is threaded in the first suture anchor in the first direction. In a first alternative embodiment, the first suture anchor 200 is a check valve (not illustrated) that allows the suture 100 to be threaded in a first direction through the first suture anchor 200, but does not allow the suture 100 to be pulled back in a second direction, opposite to the first direction.

In another embodiment, the suture is a barbed suture (not illustrated) including arrow heads, or half-arrow heads such as the barb on a fishing hook, disposed at predetermined intervals along the length of the suture. Similar to the check valve, the arrow heads allow the suture to be threaded in a first direction through the first suture anchor, but the arrow heads do not allow the suture to be pulled backing a second direction, opposite to the first directions.

In yet another embodiment, the first suture anchor is shaped in a substantially figure eight shape (not illustrated). A top half of the figure eight defines an upper chamber of the first suture anchor and a bottom half of the figure eight defines a lower chamber of the first suture anchor. The suture is passed through the lower chamber of the first suture anchor. When the suture is pulled through the first suture anchor, the suture slips into the upper chamber, which secures and locks the position of the suture. In other words, once the suture enters the upper chamber, it cannot go back down to the lower chamber and thus, the suture cannot be loosened.

In another embodiment, the second suture anchor 250 may be a suture anchor 1000 including an anchor body 1010 and a plug 1020, as illustrated in FIGS. 4-7. Aspects of the configuration of the suture anchor 1000 are described in U.S. Pat. No. 8,202,295 and U.S. Patent Publication No. 2008/0077161, both of which are hereby incorporated by reference, in their entirety, for any and all purposes.

Referring to FIGS. 4-7, the suture anchor 1000 includes an anchor body 1010 and a plug 1020. The anchor body 1010 has a central region, or well, that is bored out to accept the anchor plug 1020. The well is surrounded by a wall having an outer surface 1017, an inner surface 1018, and a top surface 1016. The well also has a bottom inner surface (i.e. the bottom of the well), and a bottom outer surface (i.e. the bottom of the anchor body 1010). The inner surface 1018 of the anchor body 1010 may have threads 1015 to accept corresponding threads 1023 on the anchor plug 1020. The top edge of the inner surface 1018 of the wall, proximal to the top surface 1016, may have a bevel 1015. The outer surface 1017 of the wall may have rungs or ridges 1014 for securing the plug 1020 in bone or other tissue. The rungs or ridges 1014 provide anchoring ability to the anchor body 1010 and the suture anchor 1000 as a whole to prevent either from readily pulling out of the bone or other tissue when tensioning a suture, or over the time of implantation in a subject. Alternatively, the bored central region of the anchor body 1010 may not be threaded, but is a smooth bore that can accept an anchor plug via a friction fit. The anchor body 1010 may accommodate sutures that are draped into the anchor body 1010, and a friction fit anchor plug is then inserted, or the anchor body 1010 may accommodate sutures that are threaded through a transverse bore 1012 in the anchor body 1010, to be secured in place by an anchor plug 1020.

The transverse bore 1012 in the anchor body 1010 is configured to receive one or more sutures to be secured by the suture anchor 1000. The transverse bore 1012 is configured proximally to the bottom of the well, such that a suture may be secured between the bottom of the well and a bottom face 1026 of the anchor plug 1020. Grooves 1013 are provided that extend from the transverse bore 1012 to a top surface 1016 of the anchor body 1010, to allow for movement of a suture through the anchor body 1010 when the anchor body 1010 is in place in a bone. Therefore, once the anchor body 1010 is driven into a bone or other tissue, with a suture threaded through the transverse bore 1012, the suture is movable in the grooves 1013. The suture may be moved to the desired tension or secured in the suture anchor 1000 by engaging the anchor plug 1020 in the anchor body 1010 and driving the anchor plug 1020 until the plug engages the suture, thereby preventing movement of the suture. The suture is secured between a bottom face 1026 of the anchor plug 1020 and the bottom of the well that is formed in the anchor body 1010.

The anchor plug 1020 may have a head 1024, a threaded post 1023 for engaging the threaded inner surface 1018 of the anchor body 1010, and a bottom face 1026 that is distal to the head 1024. The anchor plug 1020 may also have a bevel 1025 that is complementary to the bevel 1015 of the inner surface 1018. When the anchor plug 1020 is fully engaged in the anchor body 1010, the bevel 1025 is configured to engage the bevel 1015 of the inner surface 1018.

The anchor plug 1020 may also be configured to be engaged by a complementary driving device such that the anchor plug 1020 may be tightened or loosened in the anchor body 1010. The head 1024 of the anchor plug 1020 is typically shaped or has a recessed area to accommodate engagement with a driving device. For example, the anchor plug 1020 may have a hexagonal drive 1021, as shown in FIGS. 4-7, or it may have a slotted drive, a Philips drive, a square drive, a star drive, a nut drive, or other mechanism that is known to those of skill in the art for engaging a complementary drive device. The anchor plug 1020 may be configured such that the top of the head 1024 of the anchor plug 1020 is flush with the top surface 1016 of the anchor body 1010, recessed in the anchor body 1010, or above the anchor body 1010, when the anchor plug 1020 is fully engaged in the anchor body 1010.

The suture anchor 1000 allows for tightening, adjustment, or re-tensioning of a suture by tightening, loosening, re-tightening, and/or removing the anchor plug 1020 from anchor body 1010. The suture anchor 1000 also allows for securing of the suture without the tying of knots or replacement of sutures when re-tensioning is required. The suture anchor 1000 may be used for the fixation of soft tissue to bone, or of bone to bone.

The suture anchor 1000 and the plug 1020 may be made from a variety of materials known to those of skill in the art. For example, for the suture anchor 1000, the material is typically a rigid material such as a metal, a polymer, or a ceramic. Biocompatible metals include, but are not limited to stainless steel, titanium, tantalum, aluminum, chromium, molybdenum, cobalt, silver, and gold, or alloys of such metals that are known to those of skill in the art. Biocompatible polymers include, but are not limited to, high-density polyethylenes, polyurethanes, or blends of such polymers, as are known to those of skill in the art. Biocompatible polymers also include absorbable materials such as polylactic acid, polyglycolic acid, or mixtures thereof. Biocompatible ceramics include, but are not limited to alumina, silica, silicon carbide, silicon nitride, zirconia, and mixtures of any two or more thereof.

The plugs 1020 may likewise be prepared from similar metals, polymers, and ceramics, however in some embodiments, the anchor plugs are prepared from materials that may be compressed. In such embodiments, the plug material is capable of being compressed from an uncompressed state to a compressed state, prior to or during insertion of the plug into the anchor body 1010. Such compression allows for the material to recoil from the compressed state to the uncompressed state and thereby increasing the friction fit between the plug and the anchor body 1010. Such materials that may be compressed include, but are not limited to, polyethylenes, silicones, polyesters, polyurethanes, polylactic acid, polyglycolic acid, or mixtures of any two or more thereof.

The suture anchor 1000 may be used to secure sutures tensioning tissue without direct contact of tissue to bone. Examples of such uses of suture tensioning without tissue to bone contact include, but are not limited to, pelvic surgery, bladder suspension surgery, brow lift or face lift surgery, hand surgery and the like.

Methods of using the suture 100 and the suture anchor 1000 are also provided. For example, referring to FIGS. 4-7, the suture anchor 1000 is capable of adjustably retaining the suture 100. In a typical procedure, a nest, or hole, is drilled into a bone. The anchor body 1010 is then placed at the top of the nest and inserted such that the transverse bore 1012 is not obscured in the bone. The suture 100 is then threaded through a tissue to be secured, and the ends of the suture 100 are threaded through the transverse bore 1012. The anchor body 1010 may then be fully or partially driven into the nest, such that the suture 100 is guided by the grooves 1013 and is freely moving through the grooves 1013 and transverse bore 1012. The anchor plug 1020 may then be engaged in the anchor body 1010 and driven into the anchor body 1010 until the suture 100 is nearly engaged. The tension of the suture 100 may then be set by the surgeon, or other medical professional, and the anchor plug 1020 fully engaged to secure the suture 100 within the suture anchor 1000. To re-adjust the tension of the suture 100, the anchor plug 1020 may be driven in a reverse direction to loosen the anchor plug 1020, thereby allowing for free movement of the suture 100 and the process of tensioning the suture 100 may be repeated. One of ordinary skill in the art would appreciate that a plurality of sutures 100 may be used in conjunction with a single suture anchor 1000.

In another aspect, a method for the double-row, knotless repair of a soft tissue 500 using instruments described herein, is provided. The method allows for tissue repair. In some embodiments, the method allows for arthroscopic rotator cuff repair, by attempting to recreate the true native footprint of the rotator cuff of a subject.

Figure 8:
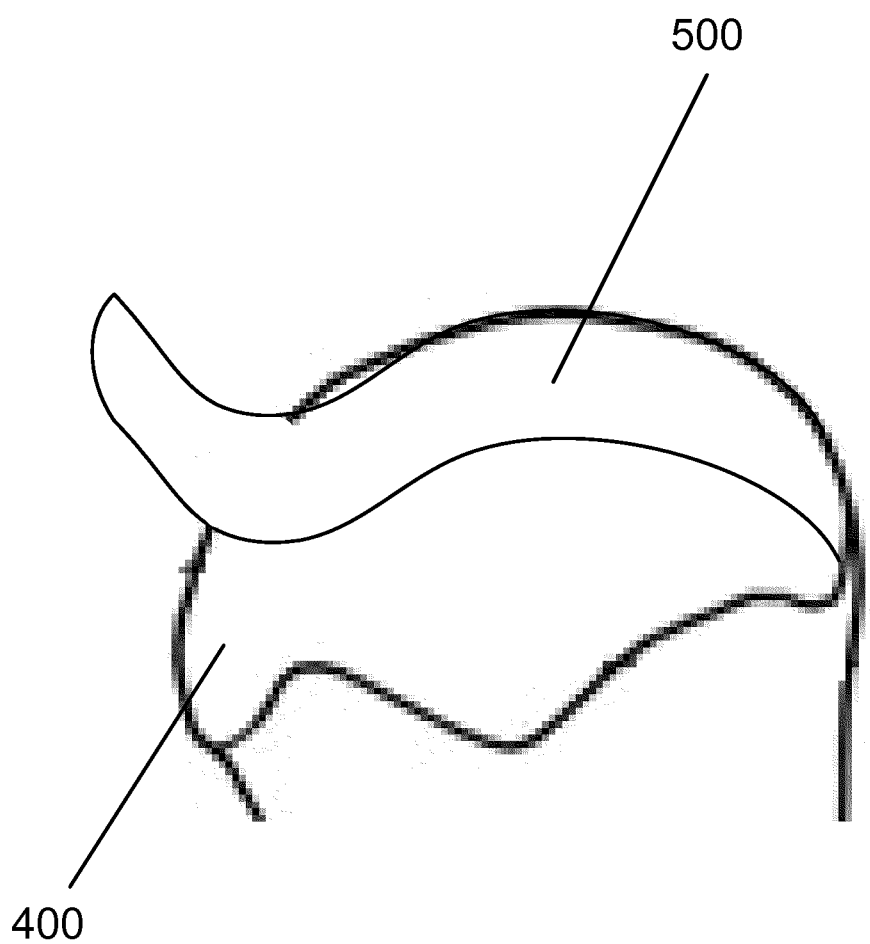
FIG. 8 is an illustration of a humerus with a soft tissue tear.
Figure 9:
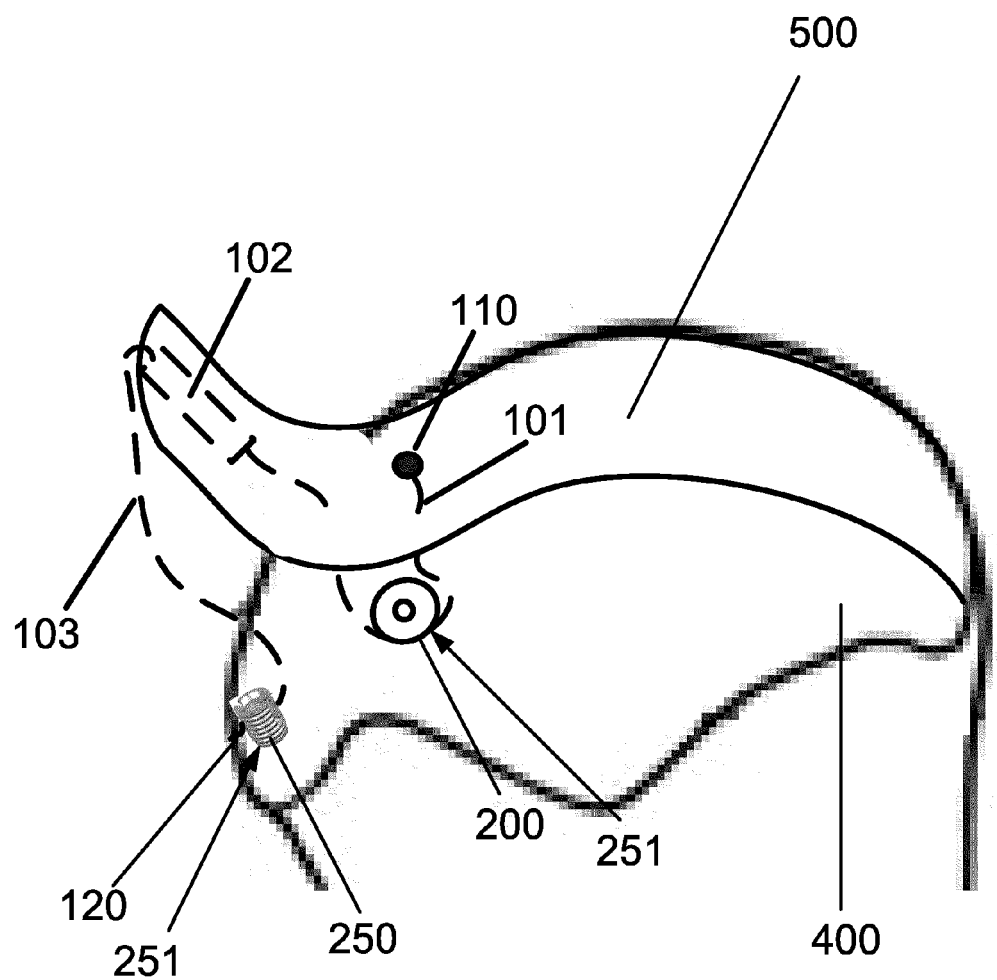
FIG. 9 is an illustration of a humerus with a system for double-row, knotless sutures to repair the soft tissue tear of FIG. 8.
Figure 10:
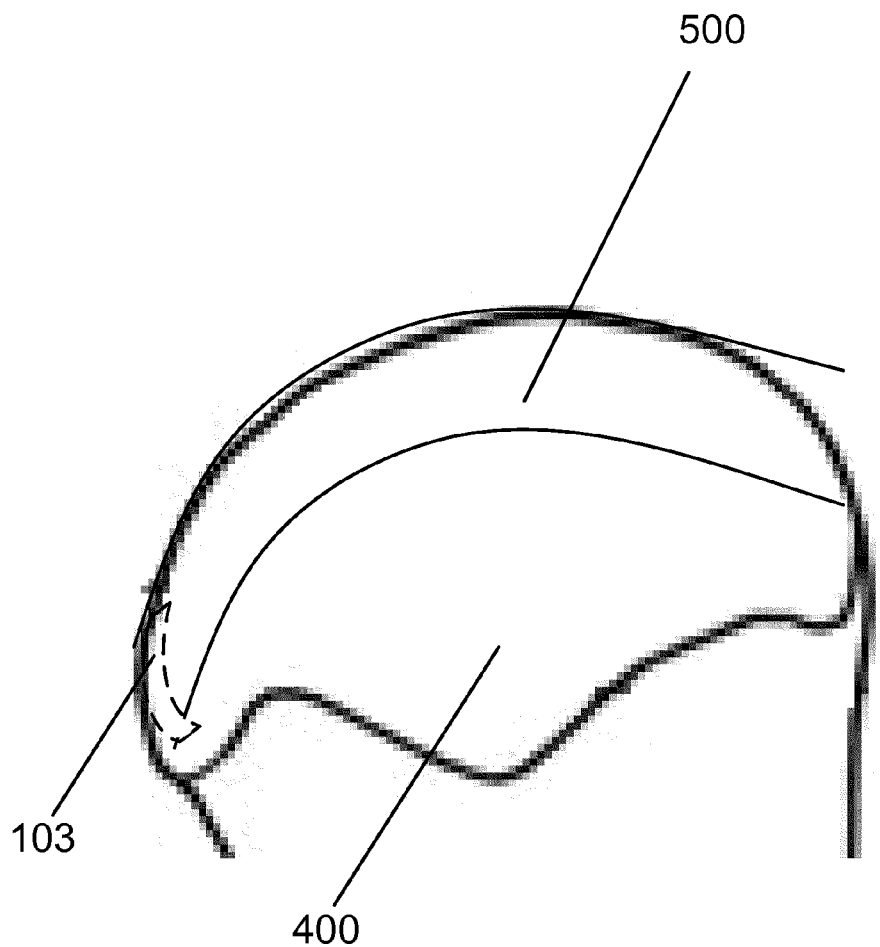
FIG. 10 is an illustration of a humerus with a suture tensioned to secure a soft tissue to the humerus to repair the soft tissue tear of FIG. 8.

Referring now to FIGS. 8-10, in some embodiments, such methods include preparing the rotator cuff bed by boring a first tunnel 201 in a portion of bone such as a humerus 400 and boring a second tunnel 251 in another portion of the humerus 400. The second tunnel 251 is disposed at a pre-determined lateral distance from the first tunnel 201. The pre-determined lateral distance between the first tunnel 201 and the second tunnel 251 is at least the length of the second region 102 of the suture 100. The first and second tunnels 201 and 251 may be bored, for example, in a greater tuberosity of the humerus 400.

The second limb 120 of the suture 100 is shuttled from the top surface of the soft tissue 500 to the bottom surface of the soft tissue 500 at a location proximate to the first tunnel 201. The first limb 110 of the suture 100 remains disposed above the soft tissue 500. The first suture anchor 200 is placed into the first tunnel 201 and fixated to the greater tuberosity of the humerus 400. The suture 100 is then passed through the humerus 400 via the first suture anchor 200. The suture 100 may be placed through the first suture anchor 200 (along the axle 2002) either before or after insertion of the first suture anchor 200 into the first tunnel 201. In this embodiment, the first suture anchor 200 is configured to serve as a pulley such that a tension of the suture 100 may be altered according to movement of the second limb 120. In other words, the first suture anchor 200 supports movement of the suture 100 along the axle 2002 in a direction of clockwise rotation of the discs 2001.

Figure 11:
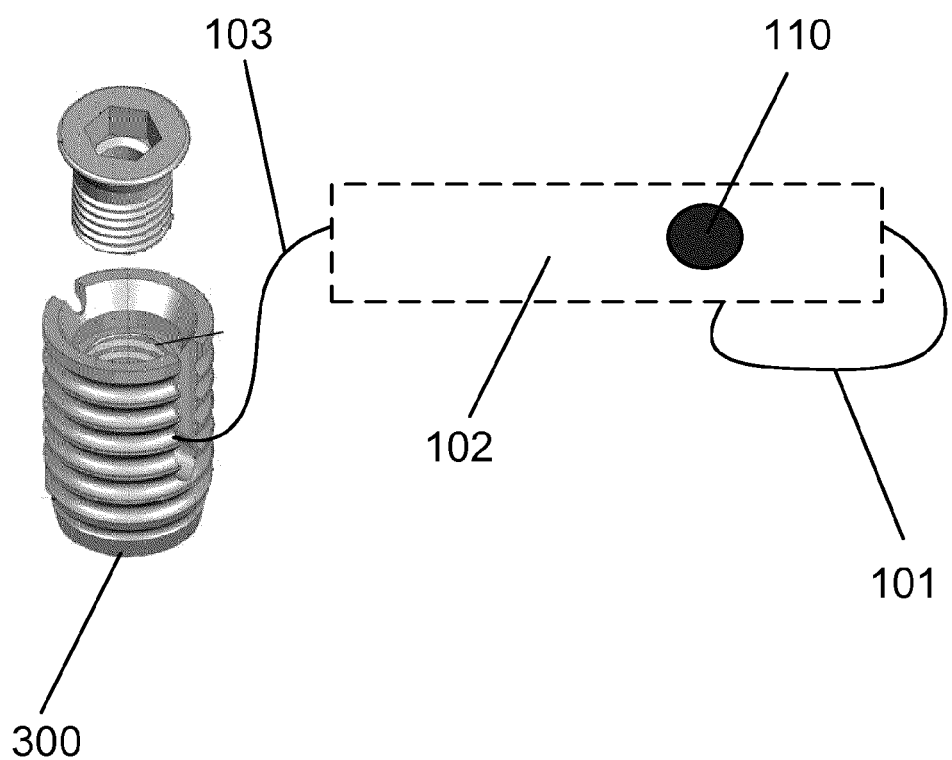
FIG. 11 is an illustration of the asymmetric suture of FIG. 1A with a first limb of the suture passed through a widened region of the suture to lock the suture upon itself.
Figure 12A:
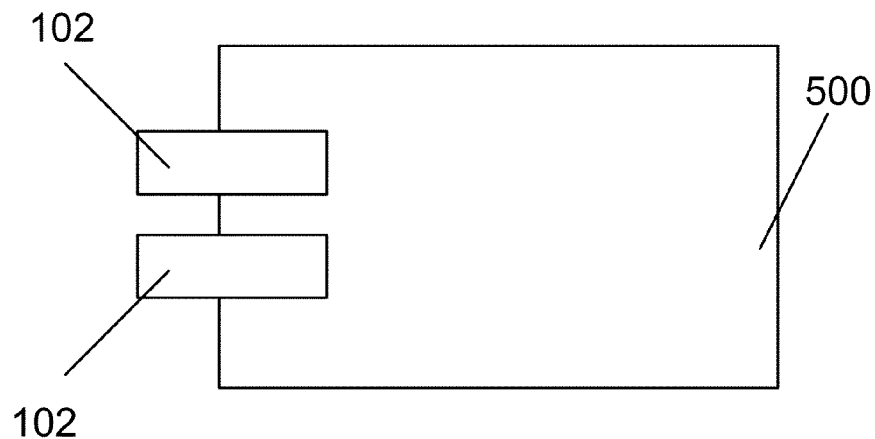
FIGS. 12A-12D are illustrations of alternate configurations including a plurality of tensioned sutures, according to alternative embodiments.
Figure 12B:
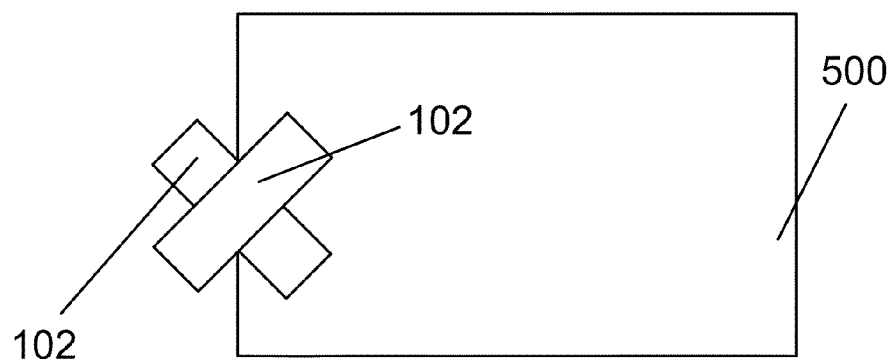
Figure 12C:
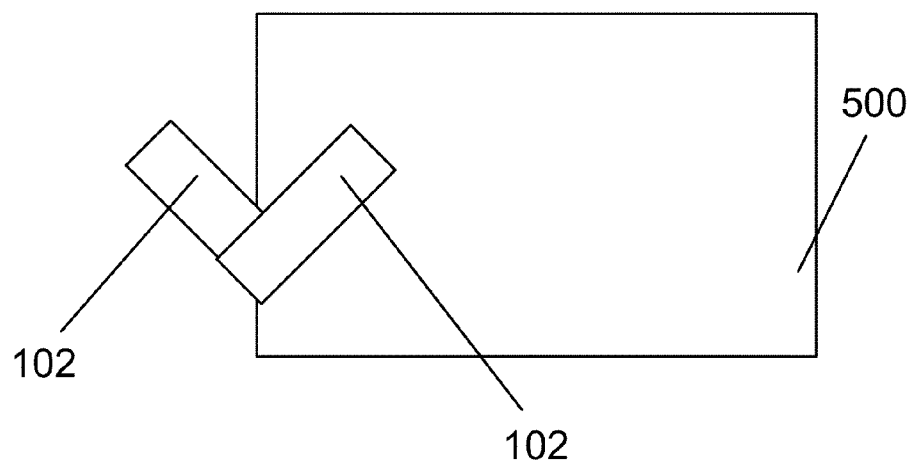
Figure 12D:
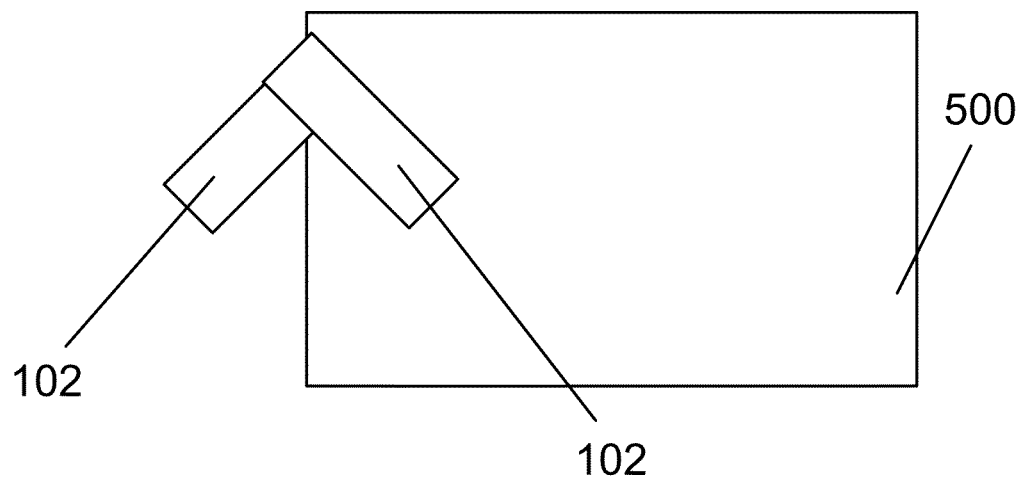

After passing through the first suture anchor 200, the second limb 120 of the suture 100 is shuttled from the bottom surface of the soft tissue 500 to the top surface of the soft tissue 500, thereby completing the medial row (i.e., the first row). At this point in the repair process, a substantial portion of the first region 101 of the suture 100 is disposed below the soft tissue 500 and within the humerus 400, while the second region 102 and the third region 103 are disposed above the soft tissue 500. The first limb 110 of the suture 100 may be passed through the second region 102, thereby creating a loose loop around the soft tissue 500 (see FIG. 11). When the first limb 110 is passed through the second region 102, the loop is sucked down over the tissue 500 and secured against the first suture anchor 200. This loop is not a knot, as it can be undone to reposition the suture 100 and/or soft tissue 500.

The second suture anchor 250 is then placed into the second tunnel 251 and fixed to the greater tuberosity of the humerus 400. The second limb 120 of the suture 100 is placed through the second suture anchor 250 without being shuttled through the soft tissue 500. Instead, the second limb 120 of the suture 100 is extended along a lateral surface of the soft tissue 500 and placed through the second suture anchor 250 either before or after insertion of the second suture anchor 250 into the second tunnel 251. At this point in the repair process, the second region 102 of the suture 100 is disposed across the top surface of the soft tissue 500, while a substantial portion of the third region 103 is disposed below the soft tissue 500 and within the humerus 400. The lateral row (i.e., the second row) is defined in part by the second region 102.

The suture 100 is then tensioned, thereby tensioning the soft tissue 500. In an embodiment in which the second suture anchor 250 is the suture anchor 1000 described above, the suture 100 may be tensioned by engaging and locking into position the anchor plug 1020 in the anchor body 1010. This step can be repeated to alter the tension of the suture 100 and therefore, re-tension the suture 100 and the soft tissue 500.

This step effectively compresses the suture 100 against the humerus 400, causes the first limb 110 to pull the proximal soft tissue 500 down against the first suture anchor 200, compresses the lateral soft tissue 500 via the second region 102 and secures the soft tissue 500 to the humerus 400.

In the method for the double-row, knotless repair of a soft tissue 500 described above, the medial suture pulls down the tissue at medial row. The medial suture is secured by the pull force of the first suture anchor 200 (i.e., the medial suture anchor) when the suture 100 is laterally secured and locked by the second suture anchor 250 (i.e., the lateral suture anchor). In other words, the suture 100 provides two points of contact (i.e., the medial and the lateral rows), but the suture 100 is only locked in at a single point (i.e., the second suture anchor 250). The second suture anchor 250 locks the suture 100, but also medially secures the medial suture. In embodiments including the loop 300, the loop 300 is provided at the first suture anchor 200, and the sides of the loop with tighten and/or lock when the suture 100 is laterally secured and locked by the second suture anchor 250.

A suture 100, a first suture anchor 200 and a second suture anchor 250 may be provided in a portable suture kit. The suture kit may contain additional instruments known in the art, for example, a scalpel, scissors, probes or forceps. The suture 100 may be a conventional suture or an asymmetrical suture according to the embodiments described above. The first suture anchor 200 may be any known suture anchor configured to allow the suture to move through the first suture anchor 200 in at least one direction. For example, the first suture anchor 200 may be the suture anchor illustrated in FIGS. 2-3. The second suture anchor 250 may be any known suture anchor configured to secure the suture. For example, the second suture anchor 250 may be the suture anchor 1000 described above, which is capable of adjustably retaining the suture 100.

One of ordinary skill in the art would appreciate that the system and methods described above can be utilized to repair any soft tissue in the body at locations proximate to bones other than the humerus. In addition, referring to FIGS. 12A-12D, one of ordinary skill in the art would appreciate that a plurality of systems could be utilized such that parallel or intersecting sets of double-row, knotless sutures may be used to repair the soft tissue. One of ordinary skill in the art would appreciate that in such alternative configurations, a plurality of suture anchors would be used in conjunction with a plurality of sutures. Any number of suture anchors and sutures may be utilized.

For the purposes of this disclosure and unless otherwise specified, "a" or "an" means "one or more."

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified. As will be understood, wherever the term "comprising" appears in the claims, it may be replaced in some embodiments with the term "consisting essentially of," or "consisting of."

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method for repairing a soft tissue comprising:
boring a first nest in a portion of a bone at a first location;
boring a second nest through a portion of the bone at a second location;
shuttling an asymmetric suture from a top surface of the soft tissue to a bottom surface of the soft tissue, the asymmetric suture being comprised of a first region proximate to a first end of the suture, an asymmetric second region, and a third region proximate to the second end of the suture, the asymmetric second region being asymmetric with respect to the first region and the third region;
disposing a first suture anchor in the first nest and fixating the first suture anchor to the first location;
passing the suture through the first suture anchor, the bottom surface of the soft tissue and the top surface of the soft tissue to form a medial row;
disposing a second suture anchor in the second nest and fixating the second suture anchor to the second location;
passing the suture through the second suture anchor from the top surface of the soft tissue such that the asymmetric second region of the suture forms a lateral row that lays across the top surface of the soft tissue to provide a greater contact area between the asymmetric suture and the soft tissue and to even a distribution of pressure on the soft tissue; and
tensioning the suture.

2. The method of claim 1, wherein
the first end of the suture is passed through an aperture in the asymmetric second region of the suture.

3. The method of claim 1, wherein the suture is defined, at least in part, by:
the first region having a first width;
the asymmetric second region having a second width; and
the third region having a third width, and
wherein the second width is greater than the first and the third widths.

4. The method of claim 1, wherein the second suture anchor that is disposed in the second nest and fixated to the second location comprises an anchor body and an anchor plug, the anchor body comprising a transverse bore, an outer surface having threads along a circumference of the suture anchor and grooves along a length of the suture anchor and an inner surface having threads configured to engage with the anchor plug.

5. The method of claim 1, wherein passing the suture through the first suture anchor comprises securing the first end of the suture to an upper surface of the soft tissue and threading the second end of the suture through a transverse bore of the first suture anchor such that the first suture anchor supports movement of the suture through the transverse bore.

6. The method of claim 1, wherein passing the suture through the second suture anchor comprises threading the second end of the suture through a transverse bore of the second suture anchor at a predetermined lateral distance from the first suture anchor, and the tensioning comprises using the second suture anchor to tension the suture along an entire length of the suture.

7. The method of claim 1, wherein the tensioning causes the soft tissue proximate to the first suture anchor to pull down against the first suture anchor, a lateral portion of the soft tissue to compress via contact with the asymmetric second region of the suture, and the soft tissue to secure to the bone.

8. The method of claim 1, wherein the tensioning comprises adjusting a tension of the suture or locking the suture by unthreading and threading an anchor plug to an anchor body of the second suture anchor.

9. The method of claim 1, wherein the lateral row and the medial row are formed without tying a knot in the suture between each row.

10. The method of claim 1, further comprising utilizing a plurality of sutures, each suture having at least one corresponding suture anchor.

11. The method of claim 1,
wherein tensioning the suture comprises receiving a portion of the suture in a suture loop comprising:
- a compressible material formed into a circular shape having a first half and a second half; and
- a plurality of teeth provided along an interior circumference of the compressible material,
- the portion of the suture being received in the compressible material; and compressing the compressible material upon itself such that the teeth provided along the interior circumference of the first half engage with the teeth provided along the interior circumference of the second half to secure the suture.

12. The method of claim 11, wherein the loop is disposed within at least one of the first suture anchor and the second suture anchor.

13. The method of claim 1,
wherein the first region of the suture has a plurality of teeth,
wherein the third region of the suture has a plurality of teeth, and
wherein tensioning the suture comprises tying the suture in a loop such that the plurality of teeth of the first region engage the plurality of teeth of the third region to secure the asymmetric second region of the suture.

* * * * *